United States Patent [19]

Heindel et al.

[11] Patent Number: 5,216,176

[45] Date of Patent: Jun. 1, 1993

[54] 7-ALKOXYCOUMARINS, DIHYDROPSORALENS, AND BENZODIPYRANONES AS PHOTO-ACTIVATED THERAPEUTIC AGENTS AND INHIBITORS OF EPIDERMAL GROWTH FACTOR

[75] Inventors: Ned D. Heindel, Easton, Pa.; Michele C. Jetter, nee Siller, Wilmington, Del.; Jeffrey D. Laskin, Piscataway; Michael A. Gallo, Belle Mead, both of N.J.

[73] Assignee: Lehigh University, Bethlehem, Pa.

[21] Appl. No.: 633,268

[22] Filed: Dec. 21, 1990

Related U.S. Application Data

[63] Continuation-in-part of Ser. No. 300,869, Jan. 23, 1989, abandoned.

[51] Int. Cl.$^5$ ............... C07D 311/78; C07D 311/02; C07D 307/77
[52] U.S. Cl. ..................... 549/280; 549/282; 549/285; 549/287; 549/288; 549/289; 549/299
[58] Field of Search ............... 549/285, 287, 288, 289, 549/282, 280, 299

[56] References Cited

U.S. PATENT DOCUMENTS

| 594,784 | 3/1974 | Heindel | 424/281 |
| 4,294,822 | 10/1981 | Kaufman | 424/59 |
| 4,950,770 | 8/1970 | Heindel | 424/281 |

OTHER PUBLICATIONS

CA 105:152961p X-ray Crystal Structure . . . Carboxylic Acid, Nakayama et al. p. 686, 1985.
V. K. Ahluwalia et al. "A Convenient Synthesis of Psoralen Derivatives: Psoralen, 4-Methyl-psoralen and 4-Phenyl-psoralen," *Monatshefte fur Chemie*, vol. 111, pp. 877-882 (1980).
P. Rodighien et al. "Synthesis of Methyl Derivatives of 8-Desmethylxanthyletine," *J. Heterocyclic Chem.* 24 p. 485 Mar. 1987.
Isaacs et al., "Synthesis and Characterization of New Psoralen Derivatives with Superior Photoreactivity and 8-Desmethylseseline, Potential Antiproliferative Agents with DNA and RNA," *Biochemistry*, vol. 16, p. 1058 (1977).
Yurow et al., "Characterization of a Photoalkylated Psoralen Receptor in Hela Cells," *J. Biological Chemistry*, 262, p. 8439-8442, Jun. 25, 1987.
Heindel et al., "Nitrations of 4',5'-Dihydropsoralens," *Journal of Heterocyclic Chemistry*, vol. 23, p. 1579 (1986).
Laskin et al., "A Possible Mechanism of Psoralen Phototoxicity Not Involving Direct Interaction with DNA," *Proc. Nat. Acad. Sci.*, vol. 82, pp. 6158-6162, Sep. 1985.

(List continued on next page.)

*Primary Examiner*—Mary C. Lee
*Assistant Examiner*—Joseph K. McKane
*Attorney, Agent, or Firm*—Ratner & Prestia

[57] ABSTRACT

A photochemotherapeutic compound of the formula

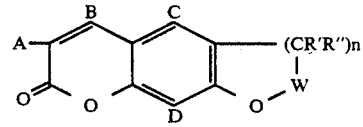

wherein
(i) n is zero, W is a ($C_{1-16}$) alkyl, alkenyl, or alkynyl linear or branched chain hydrocarbon, having no more than four O, N, or S atoms in or attached to the chain; or
(ii) n is 1, W is CR or $CR_2$, and R, R', and R" are independently H or $CH_3$; or
(iii) N is 2, W is CR or $CR_2$, and R, R', and R" are independently H or $CH_3$; and
A, B, C, and D are independently selected from hydrogen, alkyl, aryl, halogen, amino, aminoalkyl, nitro, alkoxy, aryloxy, hydroxy, carboxy, haloalkyl, or haloalkoxy, particularly compounds of the foregoing structure in which W is a charged substiuent and n=0 or 1.

11 Claims, 2 Drawing Sheets

OTHER PUBLICATIONS

Heindel et al., "Transfer Hydrogenations of Furocoumarin Derivatives," *Journal of Organic Chemistry*, vol. 48, p. 3817 (1983).

Laskin et al., "Psoralens Potentiate Ultraviolet Light-Induced Inhibition of Epidermal Growth Factor Biding," *Proc. Natl. Acad. Sci.*, vol. 83, pp. 8211, Nov. 1986.

Heindel et al., "Aminomethyl Psoralens Electrophilic Substitution of Hydroxymethylphthalimide on Linear Furocoumarins," *J. Heterocyclic Chem.*, 22, p. 73 (1985).

R. L. Edelson, "Light-Activated Drugs," *Scientific American*, Aug. 1988.

I. Willis et al., "Psoralens: A Search for More Effective Derivatives for Photochemotherapeutic Regimens," *N.C.I. Monograph* 66:143–147.

R. W. Garge, "Epidermal Ornithine Decarboxylase Activity and Thymidine Incorporation Following Treatment with Ultraviolet Light: A Combination with Topical 8-Methoxysporalen or Anthracene in the Hairless Mice," *British Journal of Dermatology*, 105:247–255 (1981).

N. Lowe et al., "Psoralen and Ultraviolet Light A Effects on Epidermal Ornithine Decarboxylase Induction and DNA Synthesis in the Hairless Mouse," *N.C.I. Monograph*, 66:73–76 (1984).

I. G. O'Brien et al., "Induction of the Polyamine Biosynthetic Enzymes in Mouse Epidermis by Tumor Promoting Agents," *Cancer Res*, 35:1662–1670 (1975).

R. S. Stern et al., "Cutaneous Squamous Cell Carcinomain Patients Treated with DUVA," *N. Eng. J. Medicine*, 310:1156–1161 (1984).

E. Biasaccia et al., "Extracorporeal Photopheresis in the Treatment of AIDS-Related Complex: A Pilot Study," *Ann. Int. Med.*, 113:270–275 (1990).

A. H. Rook et al., "Treatment of Autoimmune Disease with Extracorporeal Photochemotheraphy: Progressive Systemic Sclerosis," *The Yale J. of Biol. and Med.*, 62:639–646 (1989).

C. L. Berger, "Experimental Murine and Primate Models for Dissection of the Immunosuppressive Potential of Photochemotherapy in Autoimmune Disease and Transplantation" *Yale J. Biol. and Med.*, 62:611–620 (1989).

A. H. Rook et al., "Treatment of Autoimmune Disease with Extracorporeal Photochemotherapy: Pemphigus Vulgaris-Preliminary Report," *Yale J. Biol. and Med.*, 62:647–652 (1989).

P. W. Heald et al., "Photopheresis Therapy of Cutaneous T-Cell Lymphoma: The Yale-New Haven Experience," *Yale J. Biol. and Med.*, 62:629–638, 1985.

N. Lower et al., "Ultraviolet Light-Induces Epidermal Decarboxylase Activity," *J. Invest. Derm.*, 71:417–418 (1978).

N. J. Lower, "Ultraviolet Light and Epidermal Polyamines," *J. Invest. Derm.* 77:147–153 (1981).

7-ALKOXYCOUMARINS, DIHYDROPSORALENS, AND BENZODIPYRANONES AS PHOTO-ACTIVATED THERAPEUTIC AGENTS AND INHIBITORS OF EPIDERMAL GROWTH FACTOR

This application is a continuation-in-part of our application Ser. No. 07/300,869 filed Jan. 23, 1989, now abandoned, which has common inventorship and is assigned to the same entity as the present invention.

BACKGROUND OF THE INVENTION

A number of proliferative skin disorders such as mycosis fungoides, psoriasis, vitiligo, eczema, etc., and cancers, including cell lymphomas, may be treated by the application of photosensitizing chemicals and ultraviolet light. These procedures are known as photochemotherapy or, in the specific case of psoriasis, as PUVA (psoralens ultra violet A radiation). Chemical classes in which such phototherapeutic behavior have been observed are porphyrins, phthalocyanins, and psoralens. Each one of these classes possesses characteristics which makes it less than ideal in the phototherapeutic function: skin staining, suspected mutagenic/carcinogenic properties, poor absorption rates, and systemic toxicity.

While no single mechanism of photodermal action appears able to explain the behavior of all the known classes of photosensitizing chemicals, there is a widely-accepted mechanism for action of the three-ring heterocyclics known as psoralens or furocoumarins [S. T. Isaacs, C. J. Shen, J. E. Hearst, and H. Rapoport, Biochem., 16, 1058 (1977)]. A psoralen with the essential structural requirements indicated by the referenced mechanism is

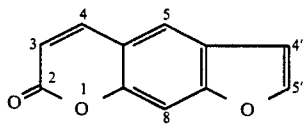

Psoralens intercalate into DNA in the cell nucleus and subsequently enter into photo-induced cross-linking with the DNA by forming 2+2, cyclobutane-like fusions from double bonds 3—4 and 4'—5' in the psoralens to double bonds in the pyrimidine bases. This molecular action in the nucleus, which requires a pair of unsaturation loci in the psoralen therapeutic, has been claimed to be the origin of the established photopharmacology. It is also the major limitation to the more wide-spread clinical use of these agents since mutagenic/carcinogenic activity is a potential side effect of DNA intercalation and subsequent alkylation or drug-linking.

SUMMARY OF THE INVENTION

This invention describes the syntheses and pharmacological properties of new photochemotherapeutics. These agents display beneficial phototherapy effects against several kinds of malignancies and demonstrate the ability to halt proliferation of a variety of cells of epidermal origin. These compounds are generally described as psoralen analogs in which either the second site of unsaturation or the tricyclic ring system is not needed for the beneficial photopharmacological effects.

The general structure of the compounds of this invention is

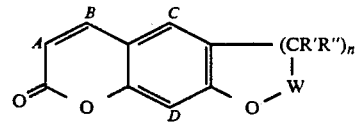

wherein i) n is zero, W is a ($C_{1-16}$) alkyl, alkenyl, or alkynyl linear or branched chain hydrocarbon, having no more than four O, N, or S atoms in or attached to the chain; or (ii) n is 1, W is CR or $CR_2$, and R, R' and R" are independently H or $CH_3$; or (iii) n is 2, W is CR or $CR_2$, and R, R', and R" are independently H or $CH_3$; and A, B, C and D are independently selected from hydrogen, alkyl, aryl, halogen, amino, aminoalkyl, nitro, haloalkoxy.

Compounds which are representative of this general structure have central cores which include:

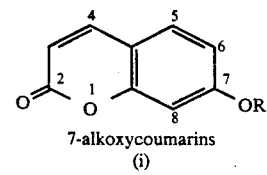

7-alkoxycoumarins
(i)

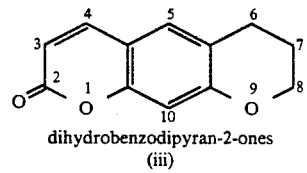

dihydrobenzodipyran-2-ones
(iii)

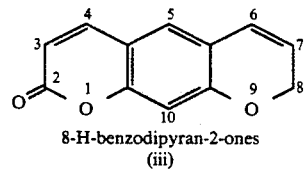

8-H-benzodipyran-2-ones
(iii)

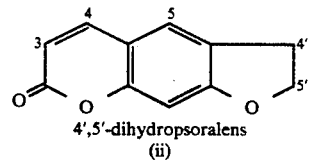

4',5'-dihydropsoralens
(ii)

Compounds of specific interest are compounds of the foregoing structures which are charged at physiologic pH in which W is or bears a charged pendant substituent. Most specifically, these include:

4,8-dimethyl-5'-(N-pyridiniummethyl) psoralen bromide 4,8-dimethyl-5'-(acetoxymethyl) psoralen 4,8-dimethyl-5'-(ethoxymethyl) psoralen 4,8-dimethyl-5'-hydroxymethylpsoralen 4,8 dimethyl-5'-bromomethylpsoralen 4,8-dimethyl-5'-(N-pyridiniummethyl) 4',5'-dihydropsoralen iodide salt 4,8-dimethyl-7-(carboxymethyloxy) coumarin 4,8-dimethyl-7-(2-N,N-dimethylaminoethoxy) coumarin 4-8-dimethyl-7-(2-N,N,N-trimethylammonium ethoxy)-coumarin iodide

DETAILED DESCRIPTION OF THE INVENTION

Figure 1:
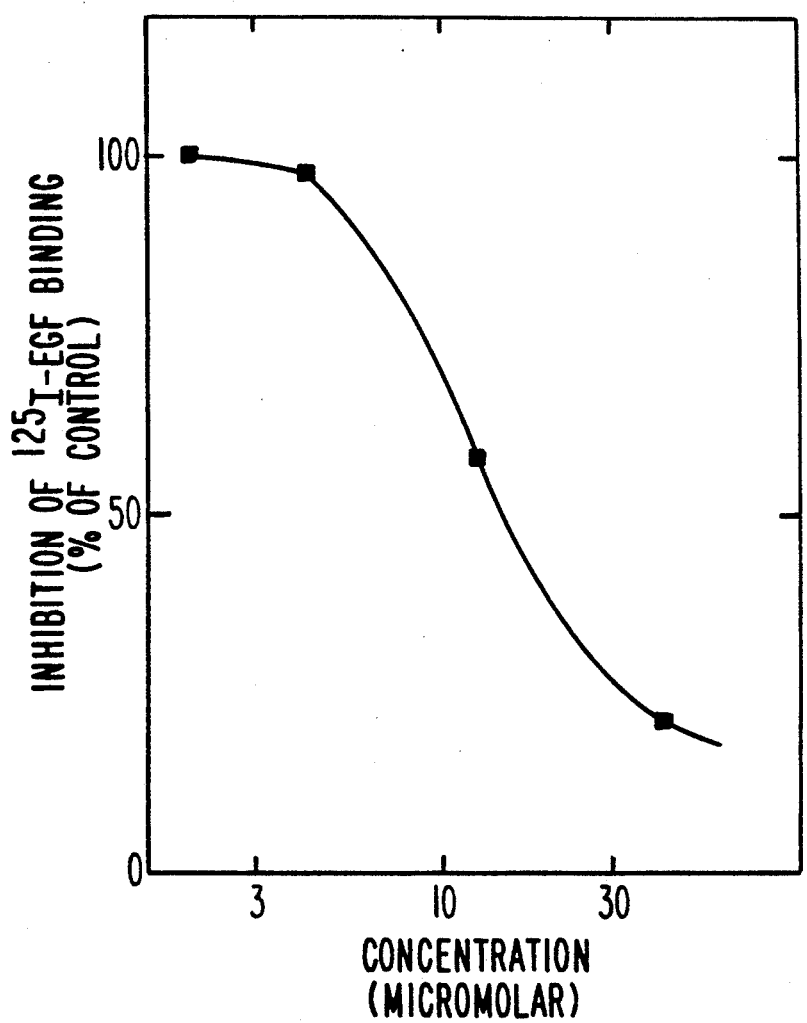

Suitable 7-alkoxycoumarin derivatives must bear an ether function at carbon #7. These side chains may have from one to 16 carbons and may be linear or branched. The side chains may specifically possess unsaturation (olefinic or acetylenic at any position) and may also possess polar functionalities such as hydroxyls, carboxyls, or amino moieties. Variation of substituents at carbon #7 alters the lipophilicity/hydrophilicity balance, apparently without modification in the site-binding properties of the pharmaceutical. Potency is minimal for the simple 7-hydroxy analogs and rises markedly for the alkyl ethers. All potent members of this group must also possess olefinic unsaturation in the pyran-2-one ring (e.g., the double bond at carbon #3). Large bulky groups at carbon #3 and/or carbon #4, which block the availability of the double bond, can reduce the activity of the compounds (e.g., 4-t-butyl, 3-nitro, 3-carboethoxy, 3,4-diphenyl).

Suitable compounds include the hydrogen-substituted (bearing no ring-bound functionalities), the monoalkyl or monoaryl substituted analogs with groups at carbons 3, 4, 5, 6, and 8; the multiply-substituted analogs with groups at more than one carbon selected from carbons 3, 4, 5, 6, and 8; and/or ether-functionalized analogs bearing such groups as methoxy, ethoxy, i-propoxy, and n-propoxy at the 5- and/or 8- positions. Alkyl and aryl groups available for attachment at ring carbons 3, 4, 5, 6, and 8 include, but are not limited to, methyl, ethyl, n-propyl, i-propyl, n- butyl, i-butyl, s-butyl, t-butyl, phenyl, and substituted phenyl.

Nitro, amino, aminomethyl, halo, carboxyl-derivative, sulfhydryl or hydroxy groups may also be present. Solubility in plasma rises for those analogs bearing carboxyl, hydroxyl, or aminomethyl (compared to a completely unsubstituted parent molecule bearing no pendant functions) and falls for those bearing nitro, halo, carboethoxy, or similar hydrophobic functionalities. Variation of such groups allows micro alteration in lipophilic/hydrophilic balance and has ultimate clinical relevance in designing candidate agents for oral versus transdermal dosage forms.

These functional groups as mentioned above may, in fact, be ionized at physiological pH and still express beneficial therapeutic potential. Some of these compounds may in fact be charged at physiologic pH naturally due to the environment. For example, the carboxy derivatives may include salts (such as COONa, COOLi, (COO)$_2$Ca, as well as sulfonic acid salts of the—SO$_3$Na variety). The amino compounds may also be protonated salts (such as —NH$_3$+ X− or —NH$_{(3-x)}$R$_x$+ X− wherein X− is any appropriate anion). The aminomethyl compounds mentioned above may be —CH$_2$—NH$_2$ or —N(CH$_3$)$_{(3-x)}$H$_x$+ and other small alkyl moieties may substitute for CH$_3$ in the latter formulation. Alternatively, a charge may be placed on a compound permanently, such as with the pyridinium group. In brief, the structural alterations which may be tolerated within these classes—in adjustment of the lipophilic/hydrophilic balance while retaining potency—can include even charged analogs.

Examples include, but are not limited to:
4,8-dimethyl-7-(carboxymethyloxy) coumarin
4,8-dimethyl-7-(2-N,N-dimethylaminoethoxy)coumarin
4-8-dimethyl-7-(2-N,N,N-trimethylammonium ethoxy) coumarin iodide
7-ethoxycoumarin
7-n-propoxycoumarin
7-n-octyloxycoumarin
4,8-dimethyl-7-(omega-carboxyheptyloxy)coumarin
4,8-dimethyl-7-allyloxycoumarin
4-methyl-8-iodo-7- (2-methyl-3-buten-2-yl)oxy coumarin
7-(2-octyn-1-yl)oxy coumarin
4-methyl-7-n-propoxycoumarin
4,8-dimethyl-7-n-propoxycoumarin Representative syntheses of these coumarin derivatives are described below. The candidate agents may be obtained by a Williamson-type ether synthesis, condensing an appropriate alkyl halide at the 7-hydroxy of the coumarin ring.

EXAMPLE 1

Synthesis of 4,8-Dimethyl-7-allyloxycoumarin

A solution of 4,8-dimethyl-7-hydroxycoumarin (4.85 g, 25.5 mmoles) in 200 ml of acetone was reacted with 3-bromopropene (4.62 g, 38.2 mmoles) in the presence of anhydrous potassium carbonate (10 g). The reaction mixture was heated under reflux for 4 hours, cooled and filtered. The collected solid was washed with fresh acetone. The filtrate and washings were combined and the solvent evaporated under reduced pressure. The crude product was recrystallized from methanol to yield the title compound as fluffy, white needles, m.p. 107°–108° C., 3.5 g, 60% yield. $^1$H NMR: 2.3 (s, 3H, C$_8$—CH$_3$), 2.4 (d, 3H, C$_4$—CH$_3$ J = 1.2 Hz), 4.6 (dt, 2H, O—CH$_2$ J = 1.5, 4.8 Hz), 5.4 (m, 2H, =CH$_2$ J = 4.8 Hz), 5.9 (m, 1H, —CH=CH$_2$), 6.1 (d, 1H, C$_3$—H, J = 1.2 Hz), 6.8 (d, 1H, C$_6$—H, J = 9.0 Hz), 7.3 (d, 1H, C$_5$—H, J = 9.0 Hz)

Anal calcd for C$_{14}$H$_{24}$O$_3$: C, 73.03; H, 6.13. Found: C, 73.02; H, 6.20.

EXAMPLE 2

Synthesis of 4-methyl-8-iodo-7-2-methyl-3-buten-2-yl)oxy coumarin

A solution of 4-methyl-8-iodo-7-hydroxycoumarin (3.86 g, 12.8 mmoles) and 3-chloro-3-methyl-1- butene (1.96 g, 19.1 mmoles) in 200 ml of acetone was heated under reflux in the presence of 8 g of anhydrous potassium carbonate for 4 hours. After it was cooled to room temperature the reaction mixture was filtered and the collected solid was washed with fresh acetone. The filtrate and washings were combined and the solvent was evaporated under reduced pressure. The yellow residue was recrystallized from methanol to yield the title compound as a powdery white solid, m.p. 151.5°–153° C., 2.56 g, 55% yield. $^1$H-NMR: 1.78 (s, 6H, CH$_3$'s), 2.4 (d, 3H, C$_4$—CH$_3$ J = 1.3 Hz), 4.65 (d, 2H, =CH$_2$ J = 6.8 Hz), 5.5 (bt, 1H, =CH J = 6.8 Hz), 6.1 (d, 1H, C$_3$—H J = 1.2 Hz), 6.8 (d, 1H, C$_6$—H J = 8.8 Hz), 7.5 (d, 1H, C$_5$—H J = 8.8 Hz).

Anal calcd for C$_{15}$H$_{15}$O$_3$I: C, 48.67; H, 4.08; I, 34.28. Found: C, 48.48; H, 3.86; 1, 34.41.

EXAMPLE 3

Synthesis of 7- (2-octyn-1-yl)oxy coumarin

A solution of 7-hydroxycoumarin (0.324 g, 1.99 mmol) and 1-bromo-2-octyne (0.378 g, 1.99 mmol) in 200 ml of acetone was heated under reflux in the presence of anhydrous potassium carbonate (3 grams) for 24 hours. After the reflux period, the reaction mixture was cooled, filtered and the collected solid was washed with fresh acetone. The acetone washings and the filtrate were combined and the solvent evaporated under reduced pressure to yield a pale yellow viscous liquid. The crude product was dissolved in a minimum amount of ethyl acetate and petroleum ether added until the solution became cloudy. The cloudy solution was concentrated under reduced pressure and a white precipitate formed. This precipitate was collected by vacuum filtration and recrystallized from aqueous methanol to yield the title compound as shiny, colorless plates, m.p. 74°–75° C., 0.245 g, 50%. $^1$H-NMR: 0.8-2.2 (m, 11H, $(CH_2)_4CH_3$), 4.7 (t, 2H, $OCH_2C$ C), 6.2 (d, 1H, $C_3$—H J=9.3 Hz), 6.8 (dd, 1H, $C_6$—H), 6.9 (d, 1H, $C_8$—H, J=2.1 Hz), 7.4 (dd, 1H, $C_5$—H, J=8.1 Hz), 7.6 (d, 1H, $C_4$—H, J=9.3 Hz).

Anal calcd for $C_{17}H_{18}O_3$: C, 75.53; H, 6.66. Found: C, 75.45; H, 6.76.

EXAMPLE 4

Synthesis of 4.8-dimethyl-7-(omega-carboxyheptyloxy)coumarin

To pentane-washed sodium hydride (0.641 g) in 20 ml of N,N-dimethyl formamide was added a solution of 4,8-dimethyl-7-hydroxycoumarin, (1.52 g, 8.00 mol) and 8-bromooctanoic acid, (1.78 g, 7.97 mol) in 20 ml of DMF dropwise with stirring. The reaction mixture was diluted with DMF to a final volume of 200 ml and heated at 80° C. (oil bath) for 16 hours. Progress of the reaction was monitored by TLC (silica, 99% $CHCl_3$:1% isopropanol). The reaction mixture was cooled, diluted with distilled $H_2O$, and acidified until pH 2. A tan precipitate formed and was collected by vacuum filtration. The crude product was treated with decolorizing carbon and recrystallized from methanol to yield the title compound as an off-white crystalline solid, m.p. 128°–130° C. 1.7 g, 68%. $^1$H-NMR: 1.2–1.8 (m, 12H, $(CH_2)_6$), 2.29 (s, 3H, $C_8$—$CH_3$), 2.38 (d, 3H, $C_4$—$CH_3$ J=0.98 Hz), 4.0 (t, 2H, O—$CH_2$), 6.1 (d, 1H, $C_3$—H J=0.98 Hz), 6.8 (d, 1H, $C_6$—H, J=8.8 Hz), 7.4 (d, 1H, $C_5$—H, J=8.8 Hz).

Anal calcd for $C_{19}H_{24}O_5$: C, 68.66; H, 7.28. Found: C, 68.43; H, 7.34.

EXAMPLE 5

Synthesis of 4,8-dimethyl-7-methoxycoumarin

A solution of 4,8-dimethyl-7-hydroxycoumarin (0.190 g, 1.00 mmol) and methyl iodide (0.180 g, 1.30 mmol) in 50 ml of dry acetone was heated at reflux in the presence of 0.5 g of potassium carbonate for 14 hours. The solution was then cooled and filtered. The filtrate was evaporated under reduced pressure to yield a beige solid. The beige solid was taken up in 20% sodium hydroxide (aqueous) and collected by vacuum filtration. The crude product was recrystallized from methanol to yield shiny white crystals, m.p. 162°–164° C., 135 mg, 66% yield. $^1$H-NMR: 2.27 (s, 3H, $C_8$—$CH_3$), 2.4 (d, 3H, $C_4$—$CH_3$, J=1.2 Hz), 3.9 (s, 3H, $OCH_3$), 6.1 (q, 1H, $C_3$—H, J=1.2 Hz), 6.8–6.9 (d, 1H, $C_6$—H, J=8.8 Hz), 7.4–7.5 (d, 1H, $C_5$—H, J=8.8 Hz).

Anal calcd for $C_{12}H_{12}O_3$: C, 70.59; H, 5.88. Found: C, 70.34; H, 5.92.

In syntheses similar to that of EXAMPLE 2 above, the following analogs were prepared:

8-iodo-7-propargyloxycoumarin, 75% yield, mp 182°–183° C.

4-methyl-8-iodo-7-(2-methyl-3-butyn-2-yloxy)coumarin, 70% yield, mp 175°–177° C.

In syntheses similar to that of EXAMPLE 1 above, the following analogs were prepared:

4,8-dimethyl-7-(carboxymethyloxy)coumarin, 61% yield, mp 122°–124° C., obtained by alkylation with chloroacetic acid;

4,8-dimethyl-7-(2-N,N-dimethylaminoethoxy) coumarin, 33% yield, low-melting solid of $R_f$ 0.55 on 1000 micron $SiO_2$ plates with 1:4 methanol:chloroform, obtained by alkylation with 2-chloro-N,N-dimethylethylamine hydrochloride salt. In a subsequent transformation the above tertiary amine can be quaternized with methyl iodide to yield;

4,8-dimethyl-7-(2-N,N,N-trimethylammonium ethoxy) coumarin iodide, 53%, m.p. 271°–273° C.

Suitable dihydrobenzodipyran-2-ones (consistent with the general structure shown) are those analogs bearing either hydrogen substitution or single alkyl or aryl group substitution at carbons 3, 4, 5, 6, 7, 8, or 10, polyalkyl or aryl substitution at these loci, and no olefinic unsaturation in the pyran ring involving carbons 6, 7, and 8. Nitro groups, halogens, aminomethyl functions and other structural moieties described above are included where their placement on the heterocyclic nucleus does not alter the fundamental structure shown. It should be noted, however, that substitution of certain polar functions at C#5 such as nitro, amino, sulfonic acid, or sulfonamide, can decrease the biologic response and such analogs are much poorer inhibitors of the binding of epidermal growth factor.

Here, too, however, the aminomethyl and other structural moieties may be protonated or quaternary and still display useful pharmacology. The structural features as noted above for peripheral attachments on the coumarins also apply to the dihydrobenzodipyran-2-one class. For example, the carboxy derivatives may include salts (such as COONa, COOLi, $(COO)_2Ca$, as well as sulfonic acid salts of the —$SO_3Na$ variety). The amino compounds may also be protonated salts (such as —$NH_3^+$ $X^-$ or —$NH_{(3-x)}R_x^+$ $X^-$ wherein $X^-$ is any appropriate anion). The aminomethyl compounds mentioned above may be —$CH_2$—$NH_2$ or —$N(CH_3)_{(3-x)}H_x^+$ and other small alkyl moieties may substitute for $CH_3$ in the latter formulation. In brief, the structural alterations which may be tolerated within these classes—in adjustment of the lipophilic/hydrophilic balance while retaining potency—can include even charged analogs.

Unsaturation appears to be necessary in the pyran-2-one ring (e.g., a double bond at carbon #3). Also included are analogs with 5- and/or 10- alkoxy substituents such as methoxy, ethoxy, i-propoxy, and n-propoxy derivatives.

Representative examples include, but are not limited to:

6,7-Dihydro-8-methyl-2H,8H-benzo[1,2-b;5,4-b']dipyran-2-one 6,7-Dihydro-4-methyl-2H,8H-benzo[1,2-b;5,4-b']dipyran-2-one 6,7-Dihydro-4-ethyl-10-n-propyl-2H,8H-benzo[1,2-b;5,4-b']-dipyran-2-one 6,7-Dihydro-8,8-diethyl-2H,8H-benzo[1,2-b;5,4-b']dipyran-2-one 6,7-Dihydro-4,6,8,8-tetramethyl-2H,8H-benzo[1,2-b;5,4-b']-dipyran-2-one 6,7-Dihydro-4-ethyl-8,8,10-trimethyl-2H,8H-benzo[1,2-b;5,4-b']-dipyran-2-one Two convenient synthetic methods of choice exist for the dihydrobenzodipyran-2-ones, hereafter designed Method A and Method B.

Method A prepares these substances by a unique catalytic selective internal hydrogen transfer reaction.

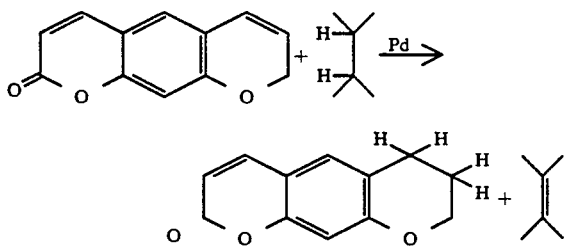

The transfer hydrogenation process itself is unexpected, facile, of high yield, and of great regiospecificity in that it exclusively reduces (under the conditions specified) the 6,7-unsaturation of 8-H-benzodipyran-2-one derivatives without reduction of the 3,4-unsaturation or the carbonyl unsaturation.

Description of the Selective Reduction Process

A solution is prepared of a suitable 8-H- benzodipyran-2-one in a low molecular weight alcohol (e.g., methanol, ethanol, i- or n-propanol) or ether (e.g., diethylether, 1,4-dioxane, tetrahydrofuran) and brought quickly to reflux. A suspension of palladium catalyst in a solution of a labile organic hydrogen donor (e.g., cyclohexene, 1,3-cyclohexadiene, 1,4- cyclohexadiene, tetralin, decalin, indane, or limonene) and an alcohol or ether is added in one portion and the resulting suspension stirred at temperatures of 50° to 150° C. for 0.5 to 10.0 hours. The mixture is filtered, evaporated, and the product isolated by crystallization, distillation, sublimation or other appropriate techniques consistent with the physical properties of the substance being isolated and well-known to chemical practitioners. Typical reactant ratios employ the hydrogen donor in 1 to 5 molar equivalents to that of the molecule to be reduced and the metal catalyst in 0.05 to 0.5 molar ratio to that of the hydrogen donor. The catalyst may be removed, washed with anhydrous methanol, dried without heating in vacuo, and re-used 10–15 times with minimal loss in reaction yields. Typical yields of the reduced products fall in the range of 40 to 75%. No hydrogen gas is required, no pressurized procedures are needed, and the reaction may be performed in ordinary laboratory glassware. If temperatures are held under ca. 80° C. and if contact times are less than 12 hours for quantities up to 10 mmoles of reducible compound, reduction of the 3, 4-double bond is not observed. Halogens, alkoxy, amino, carboxyl-derivative, and hydroxy groups survive this selective catalytic exchange hydrogenation. Nitro groups, if present, however, are reduced.

Specific examples of this method follow.

EXAMPLE 6

Preparation of 6,7-Dihydro-4,10-dimethyl-2H,8H-benzo[1,2-b;5,4-b']dipyran-2-one

A mixture of 4,10-dimethyl-2H,8H-benzo[1,2-b;5,4-b']dipyran-2-one (100 mg, 0.44 mmoles), cyclohexene (0.5 ml, 4.94 mmoles) and palladium on activated carbon (10%, 50 mg) in ethanol (25 ml) was refluxed for 5 hr. The mixture was cooled, filtered and the solvent removed under reduced pressure. The residue was recrystallized from benzene/cyclohexene to afford colorless needles of 6,7-dihydro-4,10-dimethyl-2H,8H- benzo[1,2-b;5,4-b']dipyran-2-one (40 mg, 40%), mp 162°–163° C.; $^1$H NMR 1.93, mult, 2H, H$_7$; 2.11, s, 3H, C$_{10}$— Me; 2.24, d, J=1.0 Hz, 3H, C$_4$—Me; 2.75, t, J=6.5 Hz, 2H, H$_6$; 4.20, t, J=5.2 Hz, 2H, H$_8$; 5.94, d, J=1.0 Hz, 1H, H$_3$; 6.99, s, 1H, H$_5$. $^{13}$C NMR 7.88, q, C$_{10}$—Me; 18.52, q, C$_4$—Me; 21.85, 24.86, two t, C$_6$ and C$_7$; 66.90, t, C$_8$; 111.29, d, C$_3$; 112.73, 112.84, two d, C$_{5a}$ and C$_{10}$; 118.31, s, C$_{4a}$; 122.078, d, C$_5$; 150.92, s, C$_{9a}$; 152.55, s, C$_4$; 155.74, s, C$_{10a}$; 161.54, s, C$_2$.

Anal Calcd. for C$_{14}$H$_{14}$O$_3$: C, 73.02; H, 6.12 Found: C, 72.82; H, 6.24.

Following the general synthetic method of EXAMPLE 6 representative analogs, which include but are not limited to, the substances indicated may be prepared:

6,7-dihydro-8,8-dimethyl-2H,8H-benzo[1,2-b;5,4-b']dipyran-2-one, 55% yield, mp 123°–124° C.
6,7-dihydro-4,8,8-trimethyl-2H,8H-benzo[1,2-b;5,4-b']dipyran-2-one, 48% yield, mp 174°–175° C.
6,7-dihydro-4,8,8,10-tetramethyl-2H,8H-benzo[1,2-b;5,4-b']-dipyran-2-one, 62% yield, mp 149°–150° C.

Method B: An alternative method for preparation of the dihydrobenzodipyran-2-ones involves an acid-catalyzed cyclization of either a primary allylic alcohol or a primary allylic halide with a 7-hydroxycoumarin.

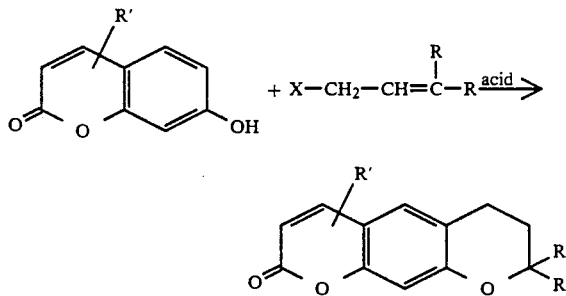

X = Leaving group
R and R' = variable functions. See NOTE under "mixtures of products" for situations in which C$_8$ bears a proton The two reactants are heated at reflux with a trace of p-toluenesulfonic acid for 2–3 hours. The solvent employed may be toluene, xylene, ethylbenzene, cumene or any other similar appropriate miscible, unreactive solvent medium known to one skilled in the art. Other sulfonic acids, e.g., methane-, benzene-, or trifluoromethanesulfonic acid may also be employed. A specific example of this method follows.

EXAMPLE 7

Preparation of 6,7-Dihydro-4,8,8,10-tetramethyl-2H,8H-benzo[1,2-b;5,4-b']dipyran-2-one The 4,8-dimethyl-7-hydroxy- coumarin (0.95 g, 5.0 mmol), 1-chloro-3-methyl-2-butene (1.4 g, 7.5 mmol) and p-toluenesulfonic acid (0.095 g, 0.50 mmol) in 25 ml of toluene were heated at reflux with stirring for 3 hours. Suitable alternatives to the 1-chloro-3-methyl-2-butene used herein are any other 1-substituted primary allylic system with a leaving group at carbon #1 (e.g., 1-iodo-3-methyl-2-butene, 3-methyl-2-buten-1-ol, or the p-toluenesulfonyl ester of 3-methyl-2-buten-1-ol). Other higher alkyl functions in lieu of the methyl groups provide similarly suitable substrates. The reaction mixture (dark brown in color) was cooled to room temperature and the solvent was removed under reduced pressure. The residue, a dark brown oil, was flash chromatographed on silica gel using methylene chloride as eluent. Fractions were analyzed by TLC (silica: $CH_2Cl_2$), pooled and the solvent evaporated under reduced pressure. The crude product was recrystallized from aqueous methanol to yield white crystals (801 mg, 62%) mp 149°–150° C. $^1$H-NMR: 1.4 (s, 6H, $C_8$—$CH_3$'s), 1.8 (t, J=6.8 Hz, 2H, $C_6$—$CH_2$), 2.2 (s, 3H, $C_{10}$—$CH_3$), 2.4 (d, J=1.2 Hz, 3H, $C_4$—$CH_3$), 2.8 (t, J=6.8 Hz, 2H, $C_7$—$CH_2$), 6.1 (q, J=1 2 Hz, 1H, $C_3$—H), 7.1 (s, 1H, $C_5$—H).

Some representative examples of substances obtainable by this route follow.

6,7-Dihydro-8,8-dimethyl-2H,8H-benzo[1,2-b;5,4-b']dipyran-2-one, 53% yield, mp 123°–124° C.

6,7-Dihydro-4,8,8-trimethyl-2H,8H-benzo[1,2-b;5,4-b']dipyran-2-one, 51% yield, mp 174°–175° C.

Suitable 8-H-benzodipyran-2-ones are those typified by the generic structure and consist of all the structurally possible variations described previously herein for the dihydrobenzodipyran-2-ones consistent with the presence of a double bond at carbon #6. Some examples of this class include but are not limited to:

2H,8H-Benzo[1,2-b;5,4-b']dipyran-2-one
4-Methyl-2H,8H-benzo[1,2-b;5,4-b']dipyran-2-one
8,8,10-Trimethyl-2H,8H-benzo[1,2-b;5,4-b']dipyran-2-one
4,8,10-Trimethyl-2H,8H-benzo[1,2-b;5,4-b']dipyran-2-one
8,8-Dimethyl-2H,8H-benzo[1,2-b;5,4-b']dipyran-2-one
4,8,8-Trimethyl-2H,8H-benzo-1,2-b;5,4-b']dipyran-2-one
4,8,8,10-Tetramethyl-2H,8H-benzo[1,2-b;5,4-b']dipyran-2-one These materials can be obtained as previously described by Rodighiero et al., *Journal of Heterocyclic Chemistry*, 24, 485–488 (1987). This process requires the preparation of an intermediate alkynyl ether with subsequent thermal cyclization to the indicated product.

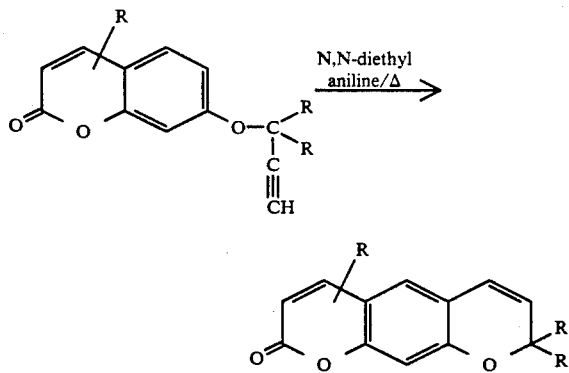

R's = H or alkyl

An improved, one-step synthesis of selected geminally-substituted analogs is disclosed in this application. An acid-catalyzed cyclization of a propargyl alcohol, or alternatively, a halide or similarly functionalized tertiary-carbon alkyne with a leaving group on the tertiary carbon seat, with a 7-hydroxy-coumarin yields 8-H-benzodipyran-2-ones in good yield without isolation of any intermediate species and without the use of elevated temperatures which induce char and tar formation. The substances available by this route fall into the structural subtype indicated:

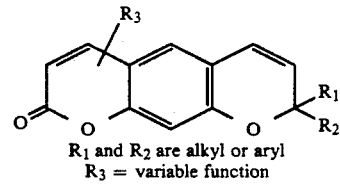

$R_1$ and $R_2$ are alkyl or aryl
$R_3$ = variable function (wherein $R_2$ and $R_3$ are methyl or higher alkyl functions)

The equation for the preparation of these materials is:

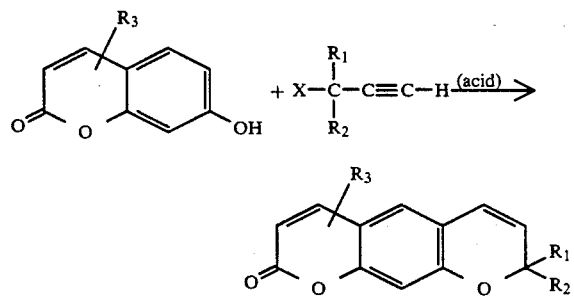

$R_1$ & $R_2$ = alkyl or aryl; $R_3$ = variable function; X = halide, OH, or other leaving group. See "mixtures of products: for case where $C_8$ bears H.

The $R_3$ variable function permits the alteration of lipophilic/hydrophilic balance and may include the range of peripheral attachments mentioned previously herein for the coumarins. The carboxy derivatives may include salts (such as COONa, COOLi, $(COO)_2Ca$, as well as sulfonic acid salts of the —$SO_3Na$ variety). The amino compounds may also be protonated salts (such as —$NH_3^+$ $X^-$ or —$NH_{(3-x)}R_x^+$ $X^-$ wherein $X^-$ is any appropriate anion). The aminomethyl compounds mentioned above may be —$CH_2$—$NH_2$ or —$N(CH_3)_{(3-x)}H_x^+$ and other small alkyl moieties may substitute for $CH_3$ in the latter formulation. In brief, the structural alterations which may be tolerated within these classes—in adjustment of the lipophilic/hydrophilic balance while retaining potency—can include even charged analogs.

Compounds obtainable in this fashion include, but are not limited to, the following:

8,8-Dimethyl-2H,8H-benzo[1,2-b;5,4-b']dipyran-2-one
4,8,8-Trimethyl-2H,8H-benzo[1,2-b;5,4-b']dipyran-2-one
4,8,8,10-Tetramethyl-2H,8H-benzo[1,2-b;5,4-b']dipyran-2-one
8,8,10-Trimethyl-2H,8H-benzo[1,2-b;5,4-b']dipyran-2-one
4,8,10-Trimethyl-2H,8H-benzo[1,2-b;5,4-b']dipyran-2-one Acids which prove suitable in this process are p-toluene sulfonic acid, other sulfonic acids compatible with the solvent system, and 10% sulfuric acid. Toluene, xylene and cumene are suitable solvent systems. Reflux times of 2–4 hours at temperatures of 90°–110° C. provide yields of 45–60% when hydroxycoumarin concentrations are in the 5–10 mmole range.

The method of synthesis is exemplified by the following.

EXAMPLE 8

Preparation of 8,8,10-trimethyl-2H,8H-benzo[1,2-b;5,4-b']dipyran-2-one

A solution prepared from 5.0 mmol of 8-methyl-7-hydroxycoumarin and 6.0 mmol of 2-methyl-3-butyn-2-ol in 40 ml of xylene containing 0.095 g (0.50 mmol) of p-toluenesulfonic acid was refluxed with magnetic stirring for 4 hours. The solvent was distilled off in vacuo and the oily contents of the flask chilled in an ice-salt water bath to induce crystallization. The white microneedles, 33% yield, were recrystallized from methanol to analytical purity, m.p. 105°–107° C. (lit. m.p. 106°–107° C.). The $^1$H-NMR spectrum was also identical to that reported, see P. Rodighiero et al., reference cited above.

When the original 7-hydroxycoumarin being employed is unsubstituted in both carbon #6 and carbon #8, mixtures of the linear isomers (benzo[1,2-b;5,4-b']dipyran-2-ones) and the angular isomer (benzo[1,2-b;3,4-b']dipyran-2-ones) result.

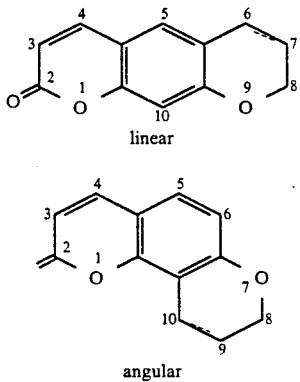

linear angular

Ring cyclization syntheses of both the 6,7-dihydro compounds and the unsaturated compounds may give rise to such mixtures if the substitution on the parent molecule permits it. ( - - - ) implies presence of an optional double bond (i.e., a linear 8-H-benzodipyran-2-one).

If linear isomers are desired this may be achieved in three ways:

(1) selection of a coumarin bearing an alkyl or aryl function in position #8 to preclude closure to the angular isomer, (2) introducing an iodide atom onto the C$_8$ position which is subsequently removed by the cyclization process. This method has been used by Ahluwalia and colleagues [*Monatsh. Chem.*, 111, 877 (1980)] to force closure in one direction;

(3) chromatographic separation of the mixture of linear and angular isomers when they do form in the reaction.

As illustrative of the latter method (chromatographic purification), a synthesis performed according to Method B is given.

EXAMPLE 9

Synthesis and Purification of 6,7-Dihydro-4,8,8-trimethyl-2H,8H-benzo[1,2-b;5,4-b']dipyran-2-one (linear isomer) and 9,10-Dihydro-4,8,8-trimethyl-2H,8H-benzo[1,2-b;3,4-b']dipyran-2-one (angular isomer)

A solution prepared from 5.0 mmol of 4-methyl-7-hydroxycoumarin, 7.5 mmol of 2-methyl-3-buten-2-ol, and 0.50 mmol of trifluoromethanesulfonic acid in 25 ml of xylene was heated with stirring at reflux for 4 hours and the solvent removed by distillation in vacuo. The crude tan solids were dissolved in a minimum amount of methylene chloride and charged to a silica gel column. With methylene chloride elutant the angular isomer elutes first [29% yield, white needles, m.p. 160°–162° C. after methanol recrystallization] followed by the linear one [36% yield, white needles, m.p. 174°–175° C. after methanol recrystallization]. The angular products can be recognized by the coupled A-B double-doublet (J =ca. 6–9 Hz) for protons on C$_5$ and C$_6$ on the benzenoid ring: $^1$H-NMR for angular isomer in CDCl$_3$ with key features for identification underlined, 1.36 (s, 6H, C$_8$—CH$_3$'s), 1.80 (t, 2H, C$_9$—CH$_2$, J=6.5 Hz), 2.40 (d, 3H, C$_4$—CH$_3$, J=1.2 Hz), 2.79 (t, 2H, C$_{10}$—CH$_2$, J=6.5 Hz), 6.12 (q, 1H, C$_3$—H, J-1.2 Hz), 6.80 (d, 1H, C$_6$—H, J=8.8 Hz), and 7.29 (d, 1H, C$_5$—H, J=8.8 Hz).

Suitable 4',5'-dihydropsoralens are those typified by the generic structure having either hydrogen substitution or single alkyl (or aryl) group substitution at carbons 3, 4, 5, 8, 4', or 5' and no olefinic unsaturation in the furan ring (involving carbons 4' and 5'). Nitro, amino, alkyloxy, aryloxy, aminomethyl, halo functions and other structural variations described previously herein for the 7-oxycoumarins, but consistent with the presence of a saturated, five-membered furan ring, are included where their placement at any carbons on the three-ring system does not alter the fundamental structure shown for the 4',5'-dihydro-psoralens. Also specifically included in this class are analogs with 5- and/or 8-alkoxy substituents such as methoxy, ethoxy, i-propoxy, and n-propoxy derivatives.

Certain highly polar groups attached at carbon #5 (e.g., nitro, amino, sulfonic acid, and sulfonamide) markedly reduce the biological activity of the class. However, as noted for the other classes, the presence of highly polar moieties (even charged such as in protonated or quaternary aminos) can be tolerated and biological activity maintained. This feature (the ability to utilize charge-carrying pendant groups) has unique potential in controlling biodistribution and bioavailability of the agents. The carboxy derivatives may include salts (such as COONa, COOLi, (COO)$_2$Ca, as well as sulfonic acid salts of the —SO$_3$Na variety). The amino compounds may also be protonated salts (such as—NH$_3$+ X$^-$ or —NH$_{(3-x)}$R$_x$+ X$^-$ wherein X$^-$ is any appropriate anion). The aminomethyl compounds mentioned above may be —CH$_2$—NH$_2$ or —N(CH$_3$)$_{(3-x)}$H$_x$+ and other small alkyl moieties may substitute for CH$_3$ in the latter formulation. In brief, the structural alterations which may be tolerated within these classes—in adjustment of the lipophilic/hydrophilic balance while retaining potency—can include even charged analogs.

Methods for the syntheses of the 4',5'-dihydropsoralens have been published, [see N. D. Heindel, N. Foster, and M. Choudhuri, *J. Org. Chem.*, 48, 3817–3819 (1983);

N. D. Heindel, N. Foster, and T. Varkey, *J. Heterocyclic Chem.*, 23, 1579–1582 (1986); and N. D. Heindel, M. Choudhuri, J. Ressner, and N. Foster, 22, 73–76 (1985)]. These techniques constitute suitable synthetic approaches to these compounds.

Following these general synthetic methods, representative analogs, which include but are not limited to, the substances indicated below may be prepared:
5-N-phthalimidomethyl-4′,5′-dihydro-8-hydroxypsoralen
5-N-phthalimidomethyl-4′,5′-dihydro-8-methoxypsoralen
3-nitro-4′,5′-dihydro-8-methoxypsoralen
3-amino-4′,5′-dihydro-8-methoxypsoralen
4,5′,8-trimethyl-4′,5′-dihydropsoralen
4,4′,8-trimethyl-4′,5′-dihydropsoralen
5-nitro-4′,5′-dihydro-8-methoxypsoralen
5-amino-4′,5′-dihydro-8-methoxypsoralen
4′,5′-dihydro-8-methoxypsoralen
4′,5′-dihydro-5-methoxypsoralen
4,5′,8-trimethyl-4′-aminomethyl-4′,5′-dihydropsoralen
4,4′,8-trimethyl-5′-aminomethyl-4′,5′-dihydropsoralen
3,5-dinitro-4′,5′-dihydro-8-methoxypsoralen
5-iodo-4′,5′-dihydro-8-methoxypsoralen
4,8-dimethyl-5′-(N-pyridiniummethyl)-4′,5′-dihydropsoralen iodide salt Incidental to the preparation of the above mentioned 4′,5′-dihydropsoralens, a unique pathway to selectively funtionalized trioxsalen (4,5′,8-trimethylpsoralen) derivatives, altered at the C5,-methyl creates a hitherto unreported type of trioxsalen.

These species are potent phototherapeutics in their own right and are useful synthetic transients in preparation of the above referenced 4′,5′-dihydro compounds by hydrogenation techniques. In this method, a free-radical bromination in the dark of 4,5′,8-trimethylpsoralen yields the 5′-bromomethyl-4,8-dimethylcoumarin. Earlier bromination studies on 4,5′,8-trimethylpsoralen gave the 4,5′,8-trimethyl-4′-bromopsoralen, 4,5′,8-trimethyl-3-bromopsoralen, or 4,5′,8-trimethyl-3,4′-dibromopsoralen, see K. D. Kaufman et al., *J. Org. Chem.*, 35, 157–160 (1970).

4,8-dimethyl-5′-bromomethylosoralen is prepared by treating 0.44 mmoles of 4,5′,8-trimethylpsoralen, 0.50 mmoles on N-bromosuccinimide and 5.0 ml of dry chloroform to 3.0 hours of reflux in a sealed, nitrogen-degased, light-shielded flask with a rubber septum cap. Four equal portions of a solution of 0.06 grams of benzoyl peroxide in dry chloroform were introduced at half-hour intervals by injection through the serum cap. At the end of the reflux period the chloroform solution was washed 3 times with 1 ml portions of saturated sodium bicarbonate, once with 1 ml distilled water, and dried over anhydrous magnesium sulfate. Evaporation and recrystallization from methanol gave a 89% yield of pale yellow crystals, mp 218°–219° C.: NMR (CDCl$_3$): 2.49 (d, 3H, C$_4$—CH$_3$, J=1.5 Hz, 2.62 (s, 3H, C$_8$—CH$_3$), 4.61 (s, 2H, CH$_2$Br), 6.26 (q, 1H, C$_3$—H J=1.5 Hz), 6.80 (s, 1H, —C$_5$—H), and 7.27 ppm (s,1H, —C$_4$,—H).

Anal Calcd. for C$_{14}$H$_{11}$BrO$_3$ ⅓ H$_2$O: C, 53.65; H, 3.76 Found: C, 53.90; H, 3.68, This versatile intermediate can be displaced with amines (e.g., pyridine), acetate, ethanol, or water to yield the corresponding:
4,8-dimethyl-5′-(N-pyridiniummethyl)psoralen bromide, 52% yield, m.p. 251°–253° C.,
4,8-dimethyl-5′-(acetoxymethyl)psoralen, 63%, m.p. 171°–173° C.,
4,8-dimethyl-5′-(ethoxymethyl)psoralen, 48% yield, m.p. 147°–148.5° C., and
4,8-dimethyl-5′-hydroxymethylpsoralen, 60% yield, m.p. 214°–216° C.

A major limiting factor in psoralen toxicity is that it enters cells and photoalkylates DNA causing mutations and cancer. 4,8-dimethyl-5′(N-pyridiniummethyl) psoralen is a unique psoralen analog in that it is charged at physiologic pH and can not cross cell membranes. It thus will not photoalkylate DNA and is unlikely to cause cancer. $^{125}$I-EGF binding data as shown in Table I indicates that it is extremely active in a cell culture model. This compound is also effective in an animal bioassay.

Effect of 4,8-dimethyl-5′(N-pyridiniummethyl) Psoralen Bromide on Epidermal Ornithine Decarboxylase in Mouse Skin Clinically, the photoactivated psoralens are active in human skin. Previous work has shown that the psoralens are active in the skin in an animal model. In this model, the psoralens in combination with ultraviolet light are potent inducers of epidermal ornithine decarboxylase activity. Ornithine decarboxylase is the rate limiting enzyme in polyamine biosynthesis and has been used as a marker for epidermal cell proliferation and biological activity of the psoralens. In this model, mice are treated with the compounds topically and then exposed to ultraviolet light (UVA). Twenty-four hours later, the mice are killed and the epidermis is isolated and assayed for ornithine decarboxylase activity.

A standard assay is used to measure enzyme activity. Briefly, epidermis is removed from treated mouse skin (SKH-1 female hairless mice, 10–12 weeks of age) and placed in 1 ml of a 50 mM solution of KH$_2$PO$_4$ (ph7.7), containing 2 mM dithiothreitol and 0.1 mM EDTA. Samples are homogenized on ice for 10 seconds using a polytron tissue homogenizer and then centrifuged at 11,000x g for 30 minutes at 4° C. Supernatants which were assayed for enzyme activity were saved and stored at −20° C. for up to one week. For enzyme assays, nine-well glass plates with 2 cm conical wells were placed in a 30° C. shaking water bath. Epidermal extracts (0.1 ml) were added to duplicate wells with 20 μl pyridoxal-5-phosphate (1,2 mM). A solution of L-ornithine (0.66 mM) with L-($^{1-14}$C) ornithine hydrochloride (60 mCi/mmol)was added to each well (10 μl/well) to initiate the reaction. Whatman GF/A glass microfiber filters (2.4 cm) were placed on top of each well and wetted with 100 μl of a saturated barium hydroxide solution (7 grams of barium hydroxide in 100 ml of water). A glass plate was placed over the 9-well dish to prevent drying of the filters. The reaction was terminated after 15 minutes by the addition of 100 μl of 2N H$_2$SO$_4$ and $^{14}$CO$_2$ adsorption was allowed to continue for 20 minutes. Filter disks were then counted for radioactivity on a Beckman scintillation counter.

Figure 2:
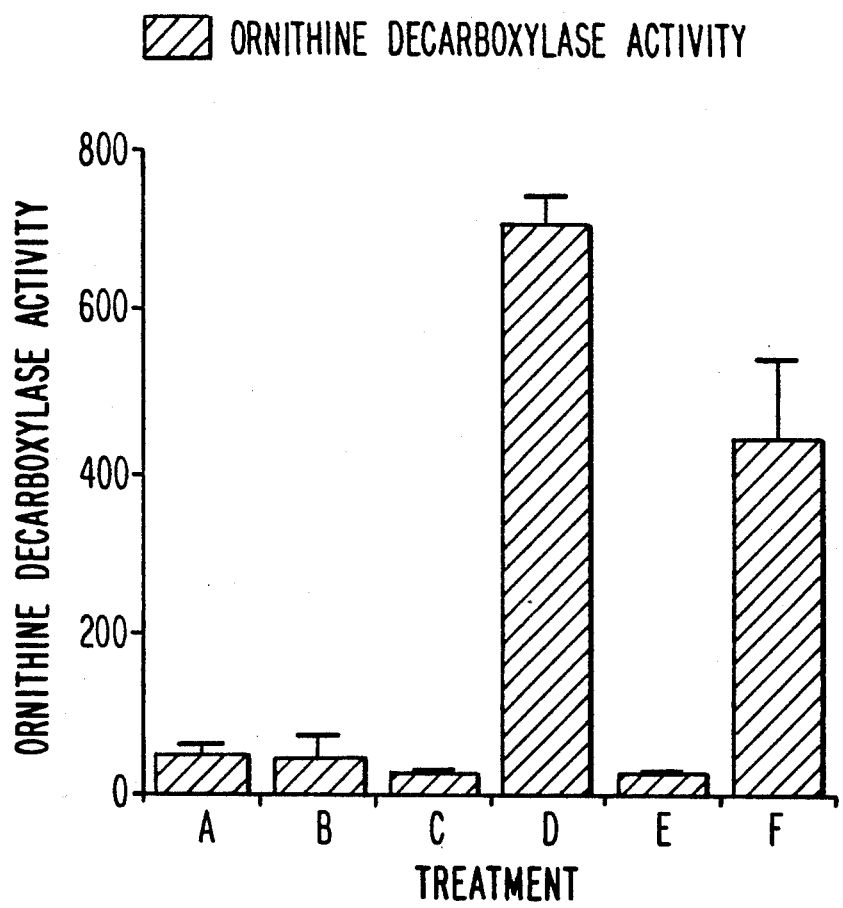

The results are shown in FIG. 2. Ornithine decarboxylase activity is presented as pmoles $^{14}$CO$_2$/mg tissue/hour. Control animals and animals treated with UVA light alone (5 J/cm$^2$) had very low activity of ornithine decarboxylase activity (treatments A and B, respectively). The psoralen analogs without UVA light (4,5′,8-trimethylpsoralen, treatment C, used as a positive control, and 4,8-dimethyl-5′(N-pyridiniummethyl) psoralen, treatment E) also had very low ornithine decarboxylase activity. Skin teated with the combination of 4,5',8-trimethylpsoralen and UVA light (treatment D) or 4,8-dimethyl-5'(N-pyridiniummethyl) psoralen and UVA light (treatment F) had very high levels of ornithine decarbosylase activity. Each value represents the average of 3 samples +standard deviation. These data demonstrate that our new compound, 4,8-dimethyl-5'(N-pyridiniummethyl) psoralen, is active in the mouse skin bioassay.

These substances mentioned above, and others which correspond to the general structure, have beneficial photo-cosmetic and photochemotherapeutic effects. The effects can be outlined as follows. In combination with light (UVA), they are able to induce a regional melanogenesis (tanning), to inhibit the binding of epidermal growth factor (EGF), and to act as anti-proliferative agents for a wide variety of cells which possess EGF receptors. It is these photoactivated properties—and their derivative clinical effects—which constitute the utility of these compounds.

The compounds are usually diluted prior to use and may be administered orally, intravenously, parenterally or topically, i.e. in the form of a lotion or ointment. The pharmaceutical compositions according to the present invention are suitable for use in effecting photochemical sensitivity on the skin of a mammal, particularly a human patient or subject, and comprise an effective amount of a compound of the invention in association with a pharmaceutically-acceptable carrier or diluent. Such compositions are well-known in the art, and reference is made to U.S. Pat. Nos. 4,124,598 and 4,130,568 for representative examples, the disclosures of which are incorporated by reference herein. The procedure for preparation of such compositions is totally conventional in the art.

For oral treatment, the active ingredient is generally formulated in tablets or in gelatin capsules. In such case the diluent may, if desired, be eliminated, although it is generally present.

For topical application, solutions or ointments may be prepared and employed. These may be formulated with any one of a number of pharmaceutically-acceptable carriers, as is well known in the art. Administration may be, for example, in the form of tablets, capsules, powders, syrups, or solutions, or as already stated in the form of ointments, creams, or solutions for topical use.

For tablet preparation, the usual tablet adjuvants such as cornstarch, potato starch, talcum, magnesium stearate, gelatin, lactose, gums, or the like may be employed, but any other pharmaceutical tableting adjuvants may also be used, provided only that they are compatible with the active ingredient.

In general, an oral dosage regimen will include about 5 mg. to about 50 mg. per kg. of body weight, with a dose in the neighborhood of about 5-10 mg. per kg. generally being preferred. Such administration and selection of dosage and unit dosage will of course have to be determined according to established medical principles and under the supervision of the physician in charge of the therapy involved.

For topical use, only an effective amount of the active ingredient per unit area is involved, and this will illustratively be in the form of a one percent solution, suspension, or ointment thereof, illustratively applied on the order of one-tenth milliliter per square centimeter, in association with a suitable carrier, e.g., ethanol, or other carrier of types already mentioned. A typical formulation for a photherapeutic lotion (1% lotion) is:

| | |
|---|---|
| propylene glycol | 25 ml |
| triethanolamine | 1 ml |
| water | 12 ml |
| oleic acid | 1.5 grams |
| polyethylene glycol 400 monostearate | 10.5 grams |
| silicon fluid DC-200 | 10 ml |
| carbopol 934, 2% mucilage | 50 grams |
| psoralen or new therapeutic | 1 gram |

Historically the uncovering of clinically-promising photherapeutics has arisen from the serendipitous discoveries of folk medicine utilization of natural products. For laboratory products, however, extensive animal trials (for which few good bioassay models exist for diseases of human skin) were required before human trials could begin. The correlations between such animal studies and human photobiology have not been uniformly promising. We have discovered that certain biochemical assays at the cellular level have preclinical predictive merit for beneficial photopharmacology. These assays are based on sound pharmacological principals of agonist-receptor interactions. [J.D. Laskin, E. Lee, E. Yurkow, D. Laskin, M. Gallo, Proc. Nat. Acad. Sci. (U.S.A.) 82: 6158(1985)].

Prior to the discovery of the methodologies described herein, structure-activity studies on the drugs disclosed and claimed in this patent would have required both extensive animal and human testing. The reason was simply that no suitable in vitro models existed for the pharmacological prescreening of large numbers of candidate phototherapeutics. Obviously, the use of live animal models is a serious limitation with regard to laboratory working-time, expense, and humane considerations. Rapid in vitro assays utilizing cells in culture are, if available, greatly advantageous, in the testing of large numbers of potential phototherapeutics. These methods, if successful, can be used as prescreens for active compounds and thereby reduce the number of substances which must eventually undergo the more systemic, in vivo, chronic toxicity/efficacy testing.

The primary in vitro screen for the phototherapeutics described in this patent is based on our discovery that beneficial phototherapeutics compete for binding in cells of epidermal origin with epidermal growth factor (EGF). Furthermore, the degree of effective competition in this EGF binding assay relates to the phototherapeutic effect of the test agent. [J. Laskin, E. Lee, D. Laskin, M. Gallo, Proc. Nat. Acad. Sci. (U.S.A.) 83: 8211 (1986)].

Epidermal growth factor is a low molecular weight polypeptide which binds to cell surface receptors and which is known to be an important regulator of growth in those cells which possess these particular cell surface receptors. Psoriasis, mycosis fungoides, eczema, cancer, and similar proliferative diseases are often characterized by abnormal cell growth regulation which may be related to the action of EGF on the cells in question. Application of PUVA therapy to correct skin disorders, especially psoriasis, is one clinical expression of photochemotherapy. The use of the assay described herein is based on the observation that phototherapeutics are extremely potent inhibitors of binding of epidermal growth factor to cell surface receptors in mammalian cells including humans and that inhibition of this binding arrests the proliferative disorder. This binding assay was performed in the cell culture laboratory.

Inhibition of EGF binding is dependent on dose of the phototherapeutic and on the quanta of light in the 320-400 nm wavelength (ultraviolet light A). It is also structure-dependent, that is, there is a direct correlation between those specific phototherapeutics currently used that are clinically active and their ability to inhibit the binding of epidermal growth factor to its receptor.

Representative examples of the compounds of the present invention, were tested in this assay for biological activity and found to be potent inhibitors of epidermal growth factor binding. Inhibition of EGF binding was rapid, dependent on concentration, and required light activation. These findings directly demonstrate that the newly synthesized compounds are potential phototherapeutics for human proliferative diseases. A description of this assay follows.

The ability of the above compounds in the presence of ultraviolet light, to inhibit epidermal growth factor binding to its cell surface receptor is directly related to its phototherapeutic potential. To assay these compounds for this biological activity, human cells (HeLa) grown in vitro were used. Cells ($1.8 \times 10^4/cm^2$) were inoculated into 5 cm culture dishes in growth medium consisting of Dulbecco's modified Eagle's medium supplemented with 10% newborn calf serum. After 4-5 days at 37° C. in a humidified $CO_2$ incubator, the cells were washed three times with 2 ml of phosphate-buffered saline and then incubated with the different phototherapeutics in 2 ml of Earle's salt solution supplemented with 5.2 mM D-glucose/25 mM Hepes buffer, pH 7.2.

Control cultures were incubated in 2 ml of Earle's salt solution in the absence of the test drugs. After 30 minutes, the cells were then exposed to ultraviolet light (UVA, 320-400 nM) emitted from a bank of four BLB fluorescent light tubes (F40BL/Sylvania) placed approximately 10 cm above the cell culture plates. The incident light delivered onto the culture plates was 3.4 mW per $cm^2$ as measured with an International Light UV-Radiometer and the cells received 2.1 $J/cm^2$ of UVA light. After this light exposure, the cells were rinsed with phosphate-buffered saline and submitted for assay of epidermal growth factor binding. Phototherapeutic treated cells were then incubated for 2 hours at 4° C. with 2 ml of binding buffer (Dulbecco's modified Eagle's medium/25 mM Hepes buffer, pH 7.2) containing 2 nM labeled epidermal growth factor ($^{125}$I-EGF, specific activity 200 Ci/g).

Nonspecific binding was determined by incubating separate plates of cells with buffer containing the radioligand and excess unlabeled epidermal growth factor (1 microgram/ml). The binding reaction of the radioligand to the cells was terminated by aspirating the binding buffer from the culture dishes and washing the cells four times with ice cold phosphate-buffered saline. The cells were then solubilized with 2 ml of 0.2M NaOH and duplicate 0.5 ml aliquots were taken for gamma counting. Specific binding of epidermal growth factor to its receptor was calculated by subtracting non-specifically bound material from the total. Under the conditions of the assay, specific epidermal growth factor receptor binding represented 80% of the total bound to the cells. The assay may be performed on a variety of cells which possess EGF receptors.

As a specific example of this assay, HeLa cells were treated with 4,8-dimethyl-7-(propargyloxy)coumarin, followed by ultraviolet light exposure and then by measurement for epidermal growth factor binding. The data can be presented as a curve of epidermal growth factor receptor binding to the cells as a percentage of untreated cells. FIG. 1 is an example of $^{125}$I-EGF binding inhibition by 4,8-dimethyl-7-(propargyloxy)coumarin) and ultraviolet light. The concentration inhibiting epidermal growth factor binding to the cells by 50% ($IC_{50}$) is determined from the curve. This is shown in Table 1 for a variety of phototherapeutics. Note that each of the compounds tested were potent inhibitors of epidermal growth factor binding to the human cells. The $IC_{50}$ values are typically in the micromolar concentration range. In the absence of ultraviolet light, these compounds did not inhibit epidermal growth factor binding. Table 1 also shows the lack of biological activity of coumarin for comparison. This is a biologically inactive analog of the phototherapeutics described in this patent. Trioxsalen, methoxysalen and 5-methoxypsoralen and other phototherapeutics currently being used in the clinic show equivalent or higher (less potent) $IC_{50}$ values in this assay.

In addition to the direct applicability of the classes of coumarins being claimed herein to photo-cosmetic and photochemotherapeutic diseases of the skin, these agents may have utility in disseminated/systemic conditions. Psoralens are now being used in a procedure known as photopheresis in which patients are administered the psoralen orally. Lymphocytes from these patients are removed and treated with ultraviolet light to activate the psoralens outside of the body. The lymphocytes are then returned to the patients.

This treatment is finding applicability in certain cancers (cutaneous T-cell lymphoma) and autoimmune diseases (scleroderma and phemphigus vulgaris). It also holds promise in suppressing immune cell rejection following transplantation. The prevailing belief is that the specific furanocoumarin structure (with double bonds in both rings and an uncharged structure to facilitate cellular uptake) is needed for these photopheresis applications. However, the currently available psoralens (mostly 8-methoxypsoralen) used in this procedure are not curative. New psoralen analogs—such as those claimed herein—may result in improved patient responses in cutaneous T-cell lymphoma, autoimmune diseases, and transplantation rejection. See, Bisaccia, E. et al., "Extracorporeal Photopheresia in the Treatment of AIDS-Related Complex: A Pilot Study." *Ann. Internal Medicine*, 113:270-275, 1990; Rook, A. H. et al., "Treatment of autoimmune disease with Extracorporeal Photochemotherapy: Progressive Systemic Scleros," *The Yale Journal of Biology and Medicine*, 62:639-646, 1989; Berger, C. L. et al., "Experimental Murine and Primate Models for Dissection of the Immunosuppressive Potential of Photochemotherapy in Autoimmune Disease and Transplantation," *The Yale J. Biol. and Med.*, 62:611-620, 1989; Rook A. H. et al., "Treatment of Autoimmune Disease with Extracorporeal Photochemotherapy: Phemphigus Vulgaris-Preliminary Report," *The Yale J. Biol. and Med.*, 62:647-652, 1989; and Heald, P. W. et al., "Photopheresis Therapy of Cutaneous T-cell Lymphoma," *The Yale J. Biol. and Med.*, 62:629-638, 1989.

TABLE 1

Comparison of the Biological Activity of Novel Phototherapeutics Using Epidermal Growth Factor Binding Inhibition Assay

| Compounds** | IC*$_{50}$ (Micromolar) |
|---|---|
| 4,5',8-trimethylpsoralen | 6.6 |
| 4',5'-dihydro-4,5',8-trimethylpsoralen | 7.0 |
| 4',5'-dihydro-3-nitro-4,5',8-trimethylpsoralen | 24 |
| 4',5'-dihydropsoralen | 11 |
| 4,8-dimethyl-7-hydroxycoumarin | 60 |
| 4,8-dimethyl-7-(propargyloxy)coumarin | 15 |
| 4,8-dimethyl-7-methoxycoumarin | 20 |
| 4,8-dimethyl-7-butyloxycoumarin | 25 |
| 6,7-dihydro-4,8,8,8,10-tetramethyl-2H,8H-benzo(1,2-b,5,4-b')dipyran-2-one | 40 |
| 6,7-dihydro-4,10-dimethyl-2H,8H-benzo(1,2-b, 5,4-b')dipyran-2-one | 7.4 |
| 6,7-dihydro-4,8,10-trimethyl-2H,8H-benzo(1,2-b, 5,4-b')dipyran-2-one | 43 |
| 4,10-dimethyl-2H,8H-benzo(1,2-b, 5,4-b')dipyran-2-one | 17 |
| 4,8-dimethyl-7-(carboxymethyloxy)coumarin | 4.4 |
| 4,8-dimethyl-7-(2-N,N,N-trimethyl-ammonium ethoxy-coumarin iodide | 30.9 |
| 4,8-dimethyl-5'-bromomethylpsoralen | 1.5 |
| 4,8-dimethyl-5'-(N-pyridiniummethyl) psoralen bromide | 0.74 |
| 4,5',8-trimethyl-4'-bromopsoralen | 1.2 |
| coumarin: | >100*** |

*IC$_{50}$, concentration of each compound inhibiting 125$_{I-EGF}$ binding to HeLa cells by 50%.
**Following treatment of the cells with phototherapeutic, they were pulsed with 2.1 J/cm$^2$ of ultraviolet light.
***Highest concentration tested.

We claim:

1. A photochemotherapeutic compound 4,8-dimethyl-7-(omega-carboxyheptyloxy) coumarin of the formula

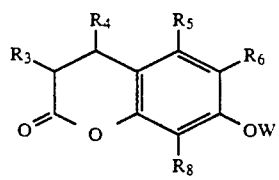

wherein W is (CH$_2$)$_7$COOH; R$_3$, R$_5$ and R$_6$ are hydrogen; and R$_4$ and R$_8$ are CH$_3$.

2. A photochemotherapeutic compound 4-methyl-8-iodo-7-(2-methyl-3-buten-2-yl)oxycoumarin of the formula

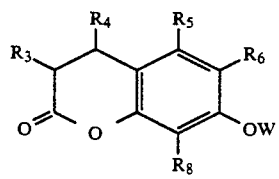

wherein W is C(CH$_3$)$_2$CH=CH$_2$; R$_3$, R$_5$ and R$_6$ are hydrogen; R$_4$ is CH$_3$; and R$_8$ is I.

3. A photochemotherapeutic compound 7-(2-octyn-1-yl)oxycoumarin of the formula

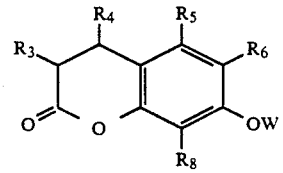

wherein W is CH$_2$C≡C(CH$_2$)$_4$CH$_3$; and R$_3$, R$_4$, R$_5$, R$_6$ and R$_8$ are hydrogen.

4. A photochemotherapeutic compound 4,8-dimethyl-7-ethoxycoumarin of the formula

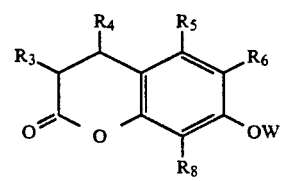

wherein W is CH$_2$CH$_3$; R$_3$, R$_5$ and R$_6$ are hydrogen; and R$_4$ and R$_8$ are CH$_3$.

5. A photochemotherapeutic compound 4,8-dimethyl-7-methoxycoumarin of the formula

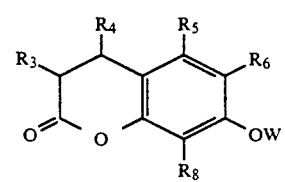

wherein W is CH$_3$; R$_3$, R$_5$ and R$_6$ are hydrogen; and R$_4$ and R$_8$ are CH$_3$.

6. A photochemotherapeutic compound 4,8-dimethyl-7-butyloxycoumarin of the formula

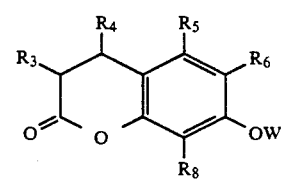

wherein W is (CH$_2$)$_3$CH$_3$; R$_3$, R$_5$ and R$_6$ are hydrogen; and R$_4$ and R$_8$ are CH$_3$.

7. A photochemotherapeutic compound of the formula:

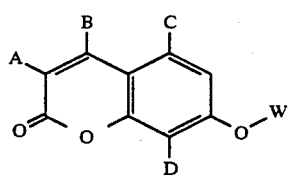

wherein
W is selected from the group consisting of a C$_1$ to C$_{16}$ alkyl and alkenyl hydrocarbon chain substituted on said hydrocarbon chain with a polar functional moiety selected from the group consisting of hydroxyl, carboxyl and amino moieties;

A, B, C, and D are independently selected from hydrogen, alkyl, aryl, halogen, amino, aminoalkyl, nitro, alkoxy, aryloxy, hydroxy, carboxy, haloalkyl, or haloalkoxy.

8. A therapeutic agent having an extracellular activity on mammalian cells comprising a pharmaceutically acceptable carrier and a compound of the formula

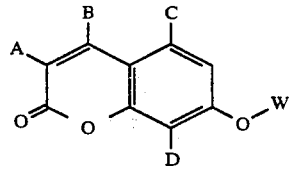

wherein

W is selected from the group consisting of a $C_1$ to $C_{16}$ alkyl and alkenyl hydrocarbon chain permissively substituted on said hydrocarbon chain with a polar functional moiety selected from the group consisting of hydroxyl, carboxyl and amino moieties, and A, B, C and D are independently selected from hydrogen, alkyl, aryl, halogen, amino, aminoalkyl, nitro, alkoxy, hydroxy, carboxy, haloalkyl or haloalkoxy.

9. A compound as recited in claim 7, wherein said compound is 4,8-dimethyl-7-(carboxymethyloxy) coumarin, wherein n=0, W=$CH_2COOH$, B=$CH_3$ and D=$CH_3$.

10. A compound as recited in claim 7, wherein said compound is 4,8-dimethyl-7-(2-N,N-dimethylaminoethoxy) coumarin, wherein n=0, W=$CH_2CH_2N(CH_3)_2$, B=$CH_3$ and D=$CH_3$.

11. A compound as recited in claim 7, wherein said compound is 4,8-dimethyl-7-(2-N,N,N-trimethylammonium ethoxy) coumarin iodide, wherein n=0, W=$CH_2CH_2N(CH_3)_3^+$ $I^-$, B=$CH_3$ and D=$CH_3$.

* * * * *

UNITED STATES PATENT AND TRADEMARK OFFICE
CERTIFICATE OF CORRECTION

PATENT NO. : 5,216,176
DATED : June 1, 1993
INVENTOR(S) : Ned. D. Heindel, Michele C. Jetter, Jeffrey D. Laskin and Michael A. Gallo It is certified that error appears in the above—identified patent and that said Letters Patent is hereby corrected as shown below:

On Cover Page, under "[75] Inventors" following "Michele C. Jetter" delete "nee Siller,".

On Cover Page, under "[56] References Cited" in the section titled "Other Publications," please correct the following prior art reference titles and/or authors as follows:

Ref. 3: Delete "P. Rogighien et al. "Synthesis of
  Methyl Derivative of 8-Desmethylxanthyletine,"
  J. Herterocyclic Chem. 24 p. 485 Mar. 1987"
  and insert therefor
  --P. Rogighiero et al., "Synthesis of Methyl
  Derivaties of 8-Desmethylxanthyletine and 8-
  Desmethylseseline, Potential Antiproliferative
  Agents," J. Heterocyclic Chem. 24, p. 485, Mar. 1987--;

Ref. 4: Delete "Isaacs et al., "Synthesis and Characterization of
  New Psoralen Derivatives with Superior Photoactivity and
  8-Desmethylseseline, Potential Antiproliferatiave Agents
  with DNA and RNA," Biochemistry, vol. 16, p. 1058 (1977) and
  insert therefor
  --Isaacs et al., "Synthesis and Characterization of New Psoralen
  Derivatives with Superior Photoreactivity with DNA and RNA,"
  Biochemistry, vol. 16, p. 1058 (1977)--;

UNITED STATES PATENT AND TRADEMARK OFFICE
CERTIFICATE OF CORRECTION

PATENT NO. : 5,216,176
DATED : June 1, 1993
INVENTOR(S) : Ned. D. Heindel, Michele C. Jetter, Jeffrey D. Laskin and Michael A. Gallo It is certified that error appears in the above—identified patent and that said Letters Patent is hereby corrected as shown below:

and

Ref. 5: Change "Yurow et al.," to --Yurkow et al.,--.

On the second page, continuation of "Other References," please continue corrections as follows:

First column, line 16, Ref. 13: Change "R. W. Garge," to
--R. W. Gange,--;

line 26, Ref. 15: Change "I. G. O'Brien et al.," to
--T. G. O'Brien et al.,--;

Second column, line 2, Ref. 16: Delete "DUVA" and insert therefor --
PUVA--;

line 4, Ref. 17: Change "E. Biasaccia et al.," to
--E. Bisaccia et al.,--;

line 23, Ref. 22: Change "N. Lower et al.," to
--N. J. Lowe et al.,--;

and line 26, Ref.: 23: Change "N. J. Lower," to
--N. J. Lowe,--.

UNITED STATES PATENT AND TRADEMARK OFFICE
CERTIFICATE OF CORRECTION

PATENT NO. : 5,216,176

DATED : June 1, 1993

INVENTOR(S) : Ned. D. Heindel, Michele C. Jetter, Jeffrey D. Laskin and Michael A. Gallo It is certified that error appears in the above—identified patent and that said Letters Patent is hereby corrected as shown below:

In the Specification

Column 4, line 1, delete
"4-8-dimethyl-7-(2-N,N,N-trimethylammonium ethoxy)
and insert therefor
--4,8-dimethyl-7-(2-N,N,N-trimethylammonium ethoxy)--.

Column 4, line 43, before "2-methyl-3-buten-2-yl)oxy"
insert --(--.

Column 5, line 24, after "4,8-dimethyl-7-(" delete
"omega-carboxyheptyloxy" and insert therefor
--omega-carboxylheptyloxy--.

UNITED STATES PATENT AND TRADEMARK OFFICE
CERTIFICATE OF CORRECTION

PATENT NO.  : 5,216,176

DATED       : June 1, 1993

INVENTOR(S) : Ned. D. Heindel, Michele C. Jetter, Jeffrey D. Laskin and Michael A. Gallo It is certified that error appears in the above—identified patent and that said Letters Patent is hereby corrected as shown below:

Column 7, lines 8 through 19, delete

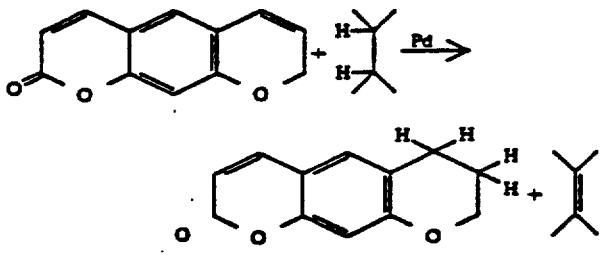

and insert therefor

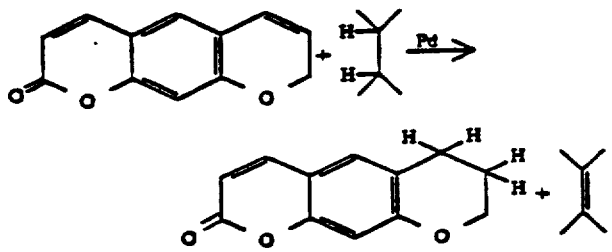

UNITED STATES PATENT AND TRADEMARK OFFICE
CERTIFICATE OF CORRECTION

PATENT NO. : 5,216,176

DATED : June 1, 1993

INVENTOR(S) : Ned. D. Heindel, Michele C. Jetter, Jeffrey D. Laskin and Michael A. Gallo It is certified that error appears in the above—identified patent and that said Letters Patent is hereby corrected as shown below:

Column 10, line 35, after "the" delete "case" and insert therefor --cases--.

Column 11, lines 29 through 45, delete

"

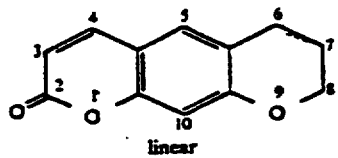
linear

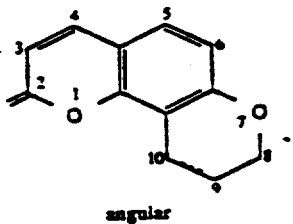
angular

"

UNITED STATES PATENT AND TRADEMARK OFFICE
CERTIFICATE OF CORRECTION

PATENT NO. : 5,216,176
DATED : June 1, 1993
INVENTOR(S) : Ned. D. Heindel, Michele C. Jetter, Jeffrey D. Laskin and Michael A. Gallo It is certified that error appears in the above—identified patent and that said Letters Patent is hereby corrected as shown below:

and insert therefor

--

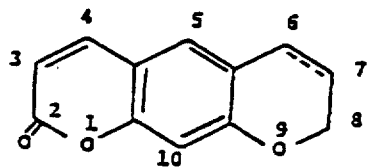

linear

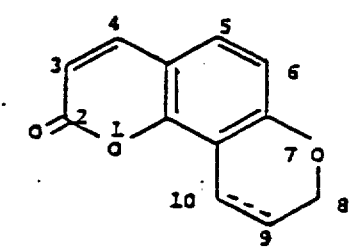

angular

--.

Column 12, lines 27 and 28, delete "6.80 (d, 1H, $C_6$ - H, J = 8.8 Hz), and 7.29 (d, 1H, $C_5$ - H, J = 8.8 Hz) and insert therefor --6.80 (d, 1H, $C_6$ - H, J = 8.8 Hz), and 7.29 (d, 1H, $C_5$ - H, J = 8.8 Hz)--.

Column 13, line 44, after "4,8-dimethyl-5'-" delete "bromomethylosoralen" and insert therefor --bromomethylpsoralen--.

UNITED STATES PATENT AND TRADEMARK OFFICE
CERTIFICATE OF CORRECTION

PATENT NO. : 5,216,176

DATED : June 1, 1993

INVENTOR(S) : Ned. D. Heindel, Michele C. Jetter, Jeffrey D. Laskin and Michael A. Gallo It is certified that error appears in the above—identified patent and that said Letters Patent is hereby corrected as shown below:

Column 14, line 47, delete "(1,2 mM)" and insert therefor --(1.2 mM)--.

Column 15, line 1, after "Skin" delete "teated" and insert therefor --treated--.

Column 15, line 5, after "ornithine" delete "decarbosylase" and insert therefor --decarboxylase--.

Column 18, line 8, after "by" delete "4,8-dimethyl-7-(propargyloxy)courmarin)" and insert therefore --4,8-dimethyl-7-(propargyloxy)courmarin--.

Column 18, line 39, after "and" delete "phemphigus" and insert therefor --pemphigus--.

Column 18, line 51, after ""Extracorporeal", delete "Photopheresia" and insert therefor --Photopheresis--.

UNITED STATES PATENT AND TRADEMARK OFFICE
CERTIFICATE OF CORRECTION

PATENT NO. : 5,216,176

DATED : June 1, 1993

INVENTOR(S) : Ned. D. Heindel, Michele C. Jetter, Jeffrey D. Laskin and Michael A. Gallo It is certified that error appears in the above—identified patent and that said Letters Patent is hereby corrected as shown below:

Column 18, line 55, after "Systemic" delete "Scleros,"
and insert therefore --Sclerosis,"--.

Column 18, line 64, after "chemotherapy:" delete
"Phemphigus" and insert therefor --Pemphigus--.

Column 19, line 2, delete "Aotivity" and insert therefor
--Activity--.

UNITED STATES PATENT AND TRADEMARK OFFICE
CERTIFICATE OF CORRECTION

PATENT NO. : 5,216,176

DATED : June 1, 1993

INVENTOR(S) : Ned D. Heindel, Michele C. Jetter, Jeffrey D. Laskin and Michael A. Gallo It is certified that error appears in the above—identified patent and that said Letters Patent is hereby corrected as shown below:

Claim 1, Column 19, lines 40 to 48, delete

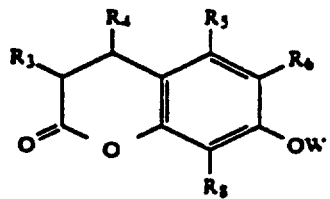

and insert therefor

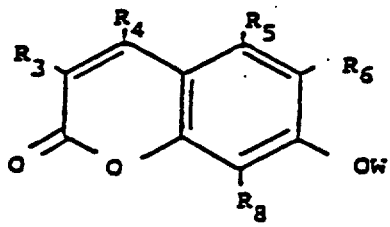

UNITED STATES PATENT AND TRADEMARK OFFICE
CERTIFICATE OF CORRECTION

PATENT NO. : 5,216,176
DATED : June 1, 1993
INVENTOR(S) : Ned D. Heindel, Michele C. Jetter, Jeffrey D. Laskin and Michael A. Gallo It is certified that error appears in the above—identified patent and that said Letters Patent is hereby corrected as shown below:

Claim 2, Column 19, lines 55 to 63, delete

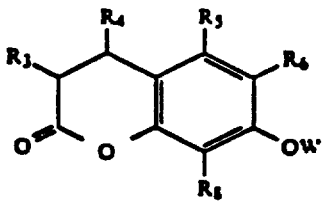

and insert therefor

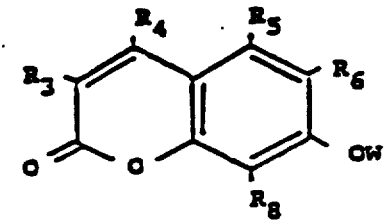

UNITED STATES PATENT AND TRADEMARK OFFICE
CERTIFICATE OF CORRECTION

PATENT NO. : 5,216,176
DATED : June 1, 1993
INVENTOR(S) : Ned D. Heindel, Michele C. Jetter, Jeffrey D. Laskin and Michael A. Gallo It is certified that error appears in the above—identified patent and that said Letters Patent is hereby corrected as shown below:

Claim 3, Column 20, lines 1 to 9, delete

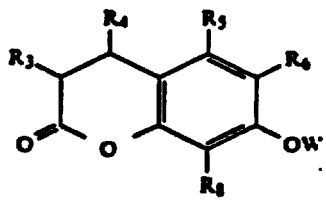

and insert therefor

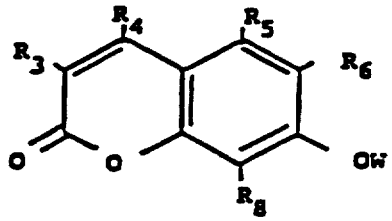

UNITED STATES PATENT AND TRADEMARK OFFICE
CERTIFICATE OF CORRECTION

PATENT NO. : 5,216,176
DATED : June 1, 1993
INVENTOR(S) : Ned D. Heindel, et al.

It is certified that error appears in the above-indentified patent and that said Letters Patent is hereby corrected as shown below:

Claim 4, Column 20, lines 15 to 23, delete

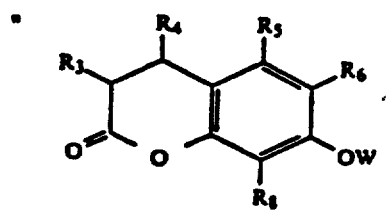

and insert therefor

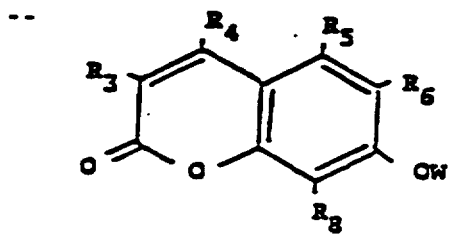

UNITED STATES PATENT AND TRADEMARK OFFICE
CERTIFICATE OF CORRECTION

PATENT NO. : 5,216,176
DATED : June 1, 1993
INVENTOR(S) : Ned D. Heindel, et al.

It is certified that error appears in the above-indentified patent and that said Letters Patent is hereby corrected as shown below:

Claim 5, Column 20, lines 41 to 48, delete

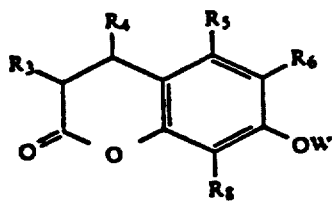

and insert therefor

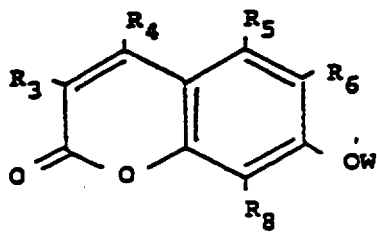

UNITED STATES PATENT AND TRADEMARK OFFICE
CERTIFICATE OF CORRECTION

PATENT NO. : 5,216,176
DATED : June 1, 1993
INVENTOR(S) : Ned D. Heindel, Michele C. Jetter, Jeffrey D. Laskin and Michael A. Gallo It is certified that error appears in the above—identified patent and that said Letters Patent is hereby corrected as shown below:

Claim 6, Column 20, lines 55 to 62, delete

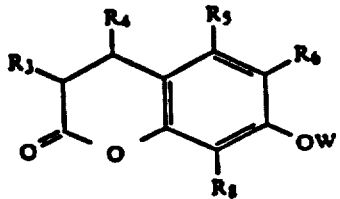

and insert therefor

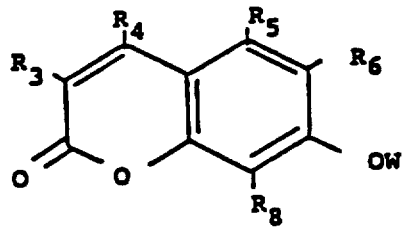

Signed and Sealed this

Eleventh Day of October, 1994

Attest:

Attesting Officer

BRUCE LEHMAN

Commissioner of Patents and Trademarks

UNITED STATES PATENT AND TRADEMARK OFFICE
CERTIFICATE OF CORRECTION

PATENT NO.    : 5,216,176
DATED         : June 1, 1993
INVENTOR(S)   : Ned D. Heindel, Michele C. Jetter,
                Jeffrey D. Laskin and Michael A. Gallo It is certified that error appears in the above-identified patent and that said Letters Patent is hereby corrected as shown below:

Column 1, line 12, insert

--This invention was made with government support under NIH Agreement ES 03467. The government has certain rights in this invention.--

Signed and Sealed this

Twentieth Day of December, 1994

Attest:

BRUCE LEHMAN

Attesting Officer    Commissioner of Patents and Trademarks